(12) United States Patent
Yamada et al.

(10) Patent No.: US 11,554,092 B2
(45) Date of Patent: Jan. 17, 2023

(54) ANTI-AGING AGENT FOR SKIN AND ANTI-AGING-RELATED GENE EXPRESSION REGULATOR

(71) Applicants: GENETIC BIO-LAB CO., LTD., Sapporo (JP); FINAL FUTURE INTERNATIONAL CO., LTD., Tokyo (JP)

(72) Inventors: Yoshihisa Yamada, Hokkaido (JP); Yuya Tada, Hokkaido (JP)

(73) Assignees: GENETIC BIO-LAB CO., LTD., Hokkaido (JP); FINAL FUTURE INTERNATIONAL CO., LTD., Tokyo (JP)

(*) Notice: Subject to any disclaimer, the term of this patent is extended or adjusted under 35 U.S.C. 154(b) by 38 days.

(21) Appl. No.: 16/652,778

(22) PCT Filed: Jul. 17, 2019

(86) PCT No.: PCT/JP2019/027998
§ 371 (c)(1),
(2) Date: Apr. 1, 2020

(87) PCT Pub. No.: WO2020/022131
PCT Pub. Date: Jan. 30, 2020

(65) Prior Publication Data
US 2020/0237636 A1 Jul. 30, 2020

(30) Foreign Application Priority Data

Jul. 24, 2018 (JP) .............................. JP2018-138405

(51) Int. Cl.
| | |
|---|---|
| *A61K 8/60* | (2006.01) |
| *A61K 8/9789* | (2017.01) |
| *A61K 31/7088* | (2006.01) |
| *A61K 36/48* | (2006.01) |
| *A61Q 19/08* | (2006.01) |

(52) U.S. Cl.
CPC ............ *A61K 8/606* (2013.01); *A61K 8/9789* (2017.08); *A61K 31/7088* (2013.01); *A61K 36/48* (2013.01); *A61Q 19/08* (2013.01)

(58) Field of Classification Search
None
See application file for complete search history.

(56) References Cited

U.S. PATENT DOCUMENTS

2008/0153741 A1   6/2008   Matsunaga et al.
2008/0161229 A1   7/2008   Matsunaga et al.

FOREIGN PATENT DOCUMENTS

| CN | 101254160 A | | 9/2008 | |
|---|---|---|---|---|
| CN | 101259084 A | | 9/2008 | |
| CN | 101371918 A | * | 2/2009 | |
| JP | 2007-291062 A | | 11/2007 | |
| JP | 2008-063315 A | | 3/2008 | |
| JP | 2008063315 A | * | 3/2008 | |
| JP | 2009-234938 A | | 10/2009 | |
| JP | 2009-234940 A | | 10/2009 | |
| JP | 2012-046544 A | | 3/2012 | |
| JP | 2018-058793 A1 | | 4/2018 | |
| KR | 10-2003-0045437 A | | 3/2005 | |
| KR | 20070099450 A | * | 10/2007 | |
| KR | 20100092925 A | * | 8/2010 | |
| KR | 10-2012-0063646 A | | 6/2012 | |
| KR | 1353628 B1 | * | 1/2014 | ............... A61K 8/02 |
| WO | WO-2007148737 A1 | * | 12/2007 | ........... A61K 8/9789 |

OTHER PUBLICATIONS

WO-2007148737-A1 translated (Year: 2007).*
CN-101371918-A translated doc (Year: 2009).*
Guncheva (Effect of Four Commonly Used Dissolution Media Surfactants on Pancreatin Proteolytic Activity, AAPS PharmSciTech, vol. 18, No. 4, May 2017) (Year: 2017).*
KR-1353628-B1 translated doc (Year: 2007).*
Lee et al., "A fermented barley and soybean formula enhances skin hydration," J. Clin. Biochem. Nutr., Jul. 30, 2015, 57(2):156-163.
Kusama et al., "About cell-activation effect of nucleic acid," Fragrance Journal, 1990, 18(4):88-91, with partial English translation.
Weng, Yujing, "The Effect of Daidzein on Collagen Synthesis and the Possible Mechanism," Master's Dissertation, East China Normal University, 2010, 82 pages, with partial English translation (Abstract and pp. 27, 28, 31,33, 36,49 and 50).
Pan, Rong Wen, "Phytoestrogen (Soy Isoflavone) can Raise and Improve Skin Quality," The 11th Southeast Asian Medical Aesthetic Conference, Aug. 8, 2007, 14-18, with partial English translation (right column of p. 14, right column of p. 15).
Moisture BB Cream, ID 2256382, Mintel GNPD [online], Dec. 2013, [Search date: Jan. 7, 2019],URL, http://www.portal.mintel.com.

(Continued)

*Primary Examiner* — Susan Hoffman
*Assistant Examiner* — Jacob A Boeckelman
(74) *Attorney, Agent, or Firm* — Foley & Lardner LLP

(57) ABSTRACT

The present invention has an object to provide a skin anti-aging agent, an agent for regulating expression of anti-aging related gene, and a cosmetic product comprising the anti-aging agent or the agent for regulating expression of anti-aging related gene which are very safe and can be used reliably for a long term. The skin anti-aging agent, the agent for regulating expression of anti-aging related gene, and the cosmetic product comprising the anti-aging agent or the agent for regulating expression of anti-aging related gene of the present invention comprise a special low molecular DNA and a soybean extract, preferably a soybean sprout extract, as active ingredients. These active ingredients have activating actions on the function of the dermal fibroblast and are hence expected to prevent or improve the skin aging such as the reduction of skin firmness and elasticity, wrinkles and sagging.

2 Claims, 1 Drawing Sheet

(56) References Cited

OTHER PUBLICATIONS

Day Serum SPF 15, ID 2339544, Mintel GNPD [online], Mar. 2014, [Search Date: Jan. 7, 2019], URL, http://www.portal.mintel.com.
Moisture Cream, ID 1684051, Mintel GNPD [online], Dec. 2011, [Search date: Jan. 7, 2019], URL, http://www.portal.mintel.com.

* cited by examiner

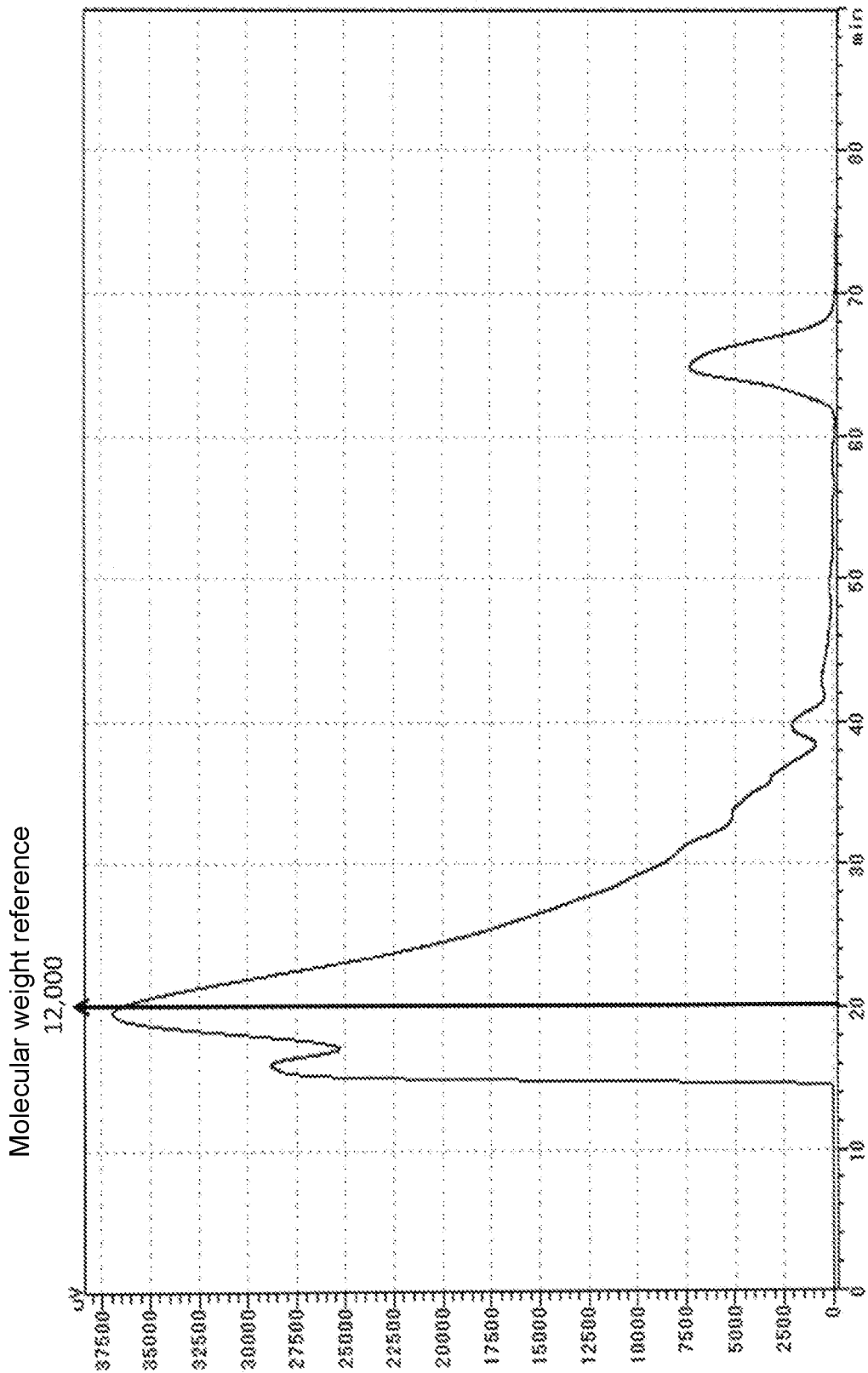

ANTI-AGING AGENT FOR SKIN AND ANTI-AGING-RELATED GENE EXPRESSION REGULATOR

CROSS-REFERENCE TO RELATED APPLICATIONS

This application is the U.S. National Stage of PCT/JP2019/027998, filed Jul. 17, 2019, which claims priority to JP 2018-138405, filed Jul. 24, 2018.

TECHNICAL FIELD

The present invention relates to skin anti-aging agents or agents for regulating expression of anti-aging related gene, and more particularly relates to a skin anti-aging agent and an agent for regulating expression of a skin anti-aging related gene comprising a special low molecular DNA and a soybean extract as active ingredients, and a cosmetic product comprising the anti-aging agent or the agent for regulating expression of anti-aging related gene.

BACKGROUND ART

Skin can be roughly divided into the epidermis which contacts the outer world, the dermis located beneath the epidermis and tightly adhered to the epidermis, and the subcutaneous adipose tissue further beneath the dermis and located between the dermis and muscles. The dermis located between the epidermis and the subcutaneous adipose tissue is constituted by the papillary layer and the reticular dermis layer, and the fibrous connective tissue. Collagen accounts for about 70% of the dermis, and besides the dermis is constituted by extracellular matrix components such as elastic fiber (elastin) and hyaluronan. Collagen, elastin, hyaluronan, and the like constituting the dermis are produced by the dermal fibroblast present in the reticular dermis layer.

These fibers are destroyed and become old due to UV ray, dryness, age advancement, and the like thereby causing their elasticity to reduce and also causing the production function of extracellular matrix components to reduce, which are generally considered as the causes of the skin aging such as the reduction of skin firmness and elasticity, wrinkles and sagging. Thus, the decrease of extracellular matrix components in the dermis, particularly collagen and hyaluronan, is involved with the aging process such as the reduction of skin elasticity and wrinkle formation.

Consequently, it is considered that the skin aging can be prevented or improved when the function of dermal fibroblast is activated and the production of extracellular matrix components described above is increased. In particular, wrinkles formed on the face have a significant impact on the person's appearance as an aging marker. For this reason, demands on cosmetic products with a wrinkle prevention or improvement effect (anti-aging and/or anti-wrinkle cosmetic products) have been increasing as a countermeasure to keep one's youth (non-patent document 1).

Here, it has been reported that deoxyribonucleic acid (DNA) used as a safe and effective functional food has an improvement effect on skin conditions (moisture level, sebum level, sulcus cutis density, wrinkle, stain, freckle, and the like) (patent documents 1, 2).

Additionally, it has been reported that an extract of soybean seeds, germs (embryos) or sprouts abundant with polyamines has a promoting action on the production of extracellular matrix components such as elastin, collagen, and hyaluronan which support the skin structure (patent document 3).

However, there has been no report on the interaction between these deoxyribonucleic acid (DNA) and the soybean extract as far as the present inventors know.

PRIOR ART DOCUMENTS

Patent Documents

[Patent Document 1] Japanese unexamined Patent Application Publication No. 2007-291062
[Patent Document 2] Japanese unexamined Patent Application Publication No. 2008-63315
[Patent Document 3] Japanese unexamined Patent Application Publication No. 2012-46544

Non-Patent Document

[Non-patent Document 1] "Development Technology of Anti-aging, Whitening, Moisturizing Cosmetics" (consumer edition), supervised by Masato Suzuki, CMC Publishing Co., Ltd., Aug. 23, 2007, First print published.

SUMMARY OF THE INVENTION

Object to be Solved by the Invention

The skin aging prevention or improvement can be expected as described above when the function of dermal fibroblast is activated and the production of extracellular matrix components, particularly collagen and hyaluronan, is increased. Accordingly, an object of the present invention is to provide a skin anti-aging agent, an agent for regulating expression of a skin anti-aging related gene, and a cosmetic product comprising the anti-aging agent or the agent for regulating expression of anti-aging related gene which have better activation effects on the dermal fibroblast and are very safe and can be used reliably for a long term.

Means to Solve the Object

The present inventors have conducted extensive studies on the above object and found that a special low molecular DNA and a soybean extract, which are safe even when taken for a long term, have synergistic activation actions on the dermal fibroblast, i.e., synergistic effects (synergy) on a cell proliferation action, a collagen production promoting action, and a hyaluronan production promoting action, synergistically promote hyaluronan synthesis-related gene expression, and also decrease hyaluronan breakdown-related gene expression. The present invention has been accomplished based on these findings. More specifically, the present invention is as follows.

(1) A skin anti-aging agent comprising: a special low molecular DNA; and a soybean extract, as active ingredients, wherein the special low molecular DNA is a hydrolysate of DNA extracted from an animal or a plant, and the soybean extract is an extract of at least one selected from the group consisting of soybean seeds, germs, and sprouts.

(2) The skin anti-aging agent according to (1), wherein the anti-aging is activation of a function of a dermal fibroblast, and the activation of the function is at least one action selected from the group consisting of a proliferation promoting action, a collagen Type I production promoting action, and a hyaluronan production promoting action on a dermal fibroblast.

(3) The skin anti-aging agent according to (1) or (2), wherein a content of the special low molecular DNA is 0.001 to 1% by mass and a content of the soybean extract is 0.001 to 1% by mass.

(4) An agent for regulating expression of a skin anti-aging related gene comprising: a special low molecular DNA; and a soybean extract, as active ingredients, wherein the special low molecular DNA is a hydrolysate of DNA extracted from an animal or a plant, and the soybean extract is an extract of at least one selected from the group consisting of soybean seeds, germs, and sprouts.

(5) The agent for regulating expression of a skin anti-aging related gene according to (4), wherein the regulation of anti-aging related gene expression is promotion of expression of at least one gene selected from the group consisting of Human Collagen Type I Alpha 1 gene, Human Hyaluronan Synthase 1 gene, and Human Hyaluronan Synthase 2 gene, or gene expression decrease of Human Matrix Metallopeptidase 1 gene and/or Human Hyaluronidase 1 gene.

(6) The agent for regulating expression of a skin anti-aging related gene according to (4) or (5), wherein a content of the special low molecular DNA is 0.001 to 1% by mass and a content of the soybean extract is 0.001 to 1% by mass.

(7) A cosmetic product comprising the skin anti-aging agent according to any one of (1) to (3), or the agent for regulating expression of a skin anti-aging related gene according to any one of (4) to (6).

Effects of the Invention

According to the present invention, a special low molecular DNA and a soybean extract, which are the active ingredients, have synergistic activation actions on the dermal fibroblast and are hence expected to prevent or improve the skin aging such as the reduction of skin firmness and elasticity, wrinkles and sagging.

BRIEF DESCRIPTION OF DRAWINGS

FIG. 1 A FIGURE showing analysis results by Gel Permeation Chromatography (GPC) on the hydrolyzed DNA-Na used in Examples. The FIGURE is plotted with retention time (min) as the horizontal axis and absorbance at a UV region (wavelength of 260 nm) as the vertical axis.

MODE OF CARRYING OUT THE INVENTION

A mode of carrying out the present invention will be described below, but the following description is only an example of the modes of carrying out the present invention, and the present invention is in no way limited to the following contents described. Note that when the expression "to" is used in the present Description, such an expression should be used to include the numerical values or physical property values before and after the expression. Additionally, a content (%) of active ingredients is weight percent (wt %) unless otherwise specified.

The skin anti-aging agent of the present invention comprises: a special low molecular DNA; and a soybean extract, as active ingredients, wherein the special low molecular DNA is a component that can be prepared by hydrolyzing DNA extracted from an animal or a plant and the soybean extract is at least one extract selected from the group consisting of soybean seeds, germs, and sprouts.

Here, the skin anti-aging means activation of a function of the dermal fibroblast, and the activation of the function means at least one action selected from the group consisting of a proliferation-promoting action, a collagen Type I production-promoting action, and a hyaluronan production-promoting action on a dermal fibroblast.

Additionally, the agent for regulating expression of a skin anti-aging related gene of the present invention comprises: a special low molecular DNA; and a soybean extract, as active ingredients, wherein the special low molecular DNA is a component that can be prepared by hydrolyzing DNA extracted from an animal or a plant and the soybean extract is at least one extract selected from the group consisting of soybean seeds, germs, and sprouts.

Here, in the present invention, the skin anti-aging related genes mean the genes encoding any of the enzymes involved with the synthesis or breakdown of collagen or hyaluronan in the dermal fibroblast described below.

Human Collagen Type I Alpha 1 gene (COL1A1)
Human Matrix Metallopeptidase 1 gene (MMP1)
Human Hyaluronan Synthase 1 gene (HAS1)
Human Hyaluronan Synthase 2 gene (HAS2)
Human Hyaluronidase 1 gene (HYAL1)

Additionally, the regulation of gene expression means the promotion of expression (increase in expression level) of the synthase genes and/or the expression decrease (decrease in expression level) of breakdown enzyme genes described above. These regulations of skin anti-aging related gene expression preferably mean promotion of expression of at least one gene selected from the group consisting of Human Collagen Type I Alpha 1 gene (COL1A1), Human Hyaluronan Synthase 1 gene (HAS1), and Human Hyaluronan Synthase 2 gene (HAS2), or gene expression decrease of Human Matrix Metallopeptidase 1 gene (MMP1) and/or Human Hyaluronidase 1 gene (HYAL1).

Further, the above-described activation of a function of a dermal fibroblast may be the above-described gene expression promotion or the above-described gene expression decrease in the dermal fibroblast.

The skin anti-aging agent or the agent for regulating expression of a skin anti-aging related gene of the present invention comprises a special low molecular DNA and a soybean extract as active ingredients, and may further comprise other optional components as needed.

The special low molecular DNA of the present invention is a component that can be prepared by hydrolyzing DNA extracted from an animal or a plant. A supply source of DNA may be various creatures such as animals, plants, and microorganisms, and a synthetic DNA may also be used as the DNA. Of these, it is particularly preferable to use DNA derived from the orchis (milt) of fish such as salmon, trout, and cod from viewpoints of abundant DNA-contained and effective utilization of wastes from processed marine products.

Extraction and purification of DNA from the fish orchis can be carried out by a routine method (for example, in accordance with the description in Japanese unexamined Patent Application Publication No. 2005-245394). For example, the fish orchis is roughly crashed, the crashed fish orchis is treated with a protein breakdown enzyme (protease) under the condition in which the DNA is not broken down, and alcohol (methanol, ethanol, isopropyl alcohol, or the like) is added to the enzymatically treated solution to precipitate the DNA in the form of a DNA salt (DNA sodium salt) and collect the precipitate. Alternatively, acid (hydrochloric acid, phosphoric acid, citric acid, or the like) is added to the enzymatically treated solution to precipitate the DNA, and the precipitate is collected, neutralized with sodium hydroxide, and dried to obtain a DNA salt (DNA sodium salt).

The obtained DNA salt is hydrolyzed using a nucleolytic enzyme such as a nuclease to obtain a special low molecular DNA. For the nuclease used for the hydrolysis treatment, for example, a nuclease derived from *Penicillium* can be used.

Hydrolysis can be carried out by, for example, charging the above DNA salt (DNA sodium salt) as a raw material to warm water adjusted to about 65° C., after stirring, further heating to 70° C., and adding a nuclease to cause the reaction. Temperature at the time of hydrolysis treatment is preferably 60 to 75° C., more preferably 70° C.

A special low molecular DNA in a powder form can be obtained by, for example, freeze-drying the obtained hydrolysate product. The special low molecular DNA by the above technique can be typically obtained in the state of a sodium salt. Note that the salt is not limited to a sodium salt, and may be, for example, a potassium salt or a calcium salt. Additionally, the special low molecular DNA may be a free form instead of a salt.

The special low molecular DNA preferably contains 10 to 80% of fractions having a molecular weight of 12,000 or less, more preferably contains 10 to 80% of fractions having a molecular weight of 5,000 or less. Note that a molecular weight distribution can be measured by classifying samples based on molecular weight using GPC followed by determining quantities using a UV detector.

The soybean extract of the present invention is at least one extract selected from the group consisting of soybean seeds, germs, and sprouts. The extraction condition is not particularly limited, but a method for obtaining a plant extract comprising polyamines, for example, as described in patent document 3, a method wherein soybean seeds, germs (embryos), or sprouts are crushed in a suitable medium and extracted under an acidic condition is preferred. Note that the germ used as a raw material may be those separated from seeds and collected, and the soybean sprout may be sprout parts collected from soybean seeds germinated under suitable conditions.

Here, polyamines are abundant in the soybean extract. Polyamine is a collective term for linear aliphatic hydrocarbons having two or more primary amino groups, present in various living bodies, and known as a growth factor involved with cell division and protein synthesis.

A polyamine content of the soybean extracts is not particularly limited but is preferably 0.05% or more, more preferably 0.1% or more, further preferably 0.15% or more, and particularly preferably 0.2% or more. Note that a polyamine content can be measured by high performance liquid chromatography.

Polyamines (putrescine, cadaverine, spermidine, spermine, and the like) are abundant in the soybean extracts, particularly an extract of the soybean sprout part (hereinafter, sometimes referred to as "soybean sprout extract") (patent document 3). When a soybean sprout extract abundant with polyamines is used, effects provided by polyamines can be expected.

A commercial product can be used as the soybean extract. Specifically, examples include soybean sprout extracts (PHYTOPOLYAMINE (registered trademark)-S (product number: SPA-301) and PHYTOPOLYAMINE-SP (product number: SPA-308)) manufactured by TOYOBO CO., LTD. and a soybean extract material (SOYPOLYA (registered trademark)) manufactured by Combi Corporation.

A content of the active ingredients in the anti-aging agent varies depending on the kind and form of a preparation, purpose of use, and frequency of use, and it is thus difficult to set a fixed content but the content and the content ratio of each component are preferably a content and a content ratio which provide synergistic effects on the activating actions on the dermal fibroblast.

For example, when the anti-aging agent is applied to skin (the anti-aging agent is a cosmetic product), the content is as follows. A content of the special low molecular DNA is preferably 0.01 to 10 mg/mL (about 0.001 to 1%), more preferably 0.01 to 5 mg/mL (about 0.001 to 0.5%), and further preferably 0.01 to 2 mg/mL (about 0.001 to 0.2%). Additionally, a content of the soybean extract is preferably 0.01 to 10 mg/mL (0.001 to 1%), more preferably 0.1 to 5 mg/mL (0.01 to 0.5%), and further preferably 0.1 to 2 mg/mL (0.01 to 0.2%).

Additionally, the content ratio of the special low molecular DNA and the soybean extract is not particularly limited but is, in terms of weight ratio, preferably the special low molecular DNA:the soybean extract=1:50 to 50:1, more preferably 1:20 to 10:1, and further preferably 1:10 to 5:1.

Further, the polyamine concentration of the anti-aging agent is determined by the kind of a preparation and product form, purpose of use, frequency of use, and the like and not particularly limited but is typically suitable to be 0.00001 to 100 mM, preferably 0.00005 to 75 mM, and more preferably 0.0001 to 50 mM.

When a content and a content ratio of the special low molecular DNA and the soybean extract are within preferable ranges, it is advantageous in the aspect of providing synergistic effects or significant effects on the activating actions (cell proliferation, collagen production promotion, hyaluronan production promotion, hyaluronan synthase gene expression promotion, hyaluronan breakdown enzyme gene expression decrease) on the dermal fibroblast as specifically described in Examples to be described later.

Here, the synergistic effects on the activating actions on the dermal fibroblast mean that when the special low molecular DNA and the soybean extract are used concurrently to the dermal fibroblast, either a cell proliferation rate, a collagen production rate, or a hyaluronan production rate is greater (significantly greater) than the sum of degrees when each component is used independently, or when the special low molecular DNA and the soybean extract are used concurrently to the dermal fibroblast, either an expression level of the collagen or hyaluronan synthase gene, preferably an expression level of the hyaluronan synthase gene, or an expression decrease level of the collagen or hyaluronan breakdown enzyme gene, preferably an expression decrease level of the hyaluronan breakdown enzyme, is greater (significantly greater) than the sum of degrees when each component is used independently. Additionally, the significant effect means an effect with a significant difference when compared to a negative control.

The anti-aging agent or the agent for regulating expression of anti-aging related gene of the present invention can be manufactured to an intended dosage form by mixing the special low molecular DNA and the soybean extract, and other components as needed by a routine method. Here, examples of the other components include the same components as optional components that the cosmetic product of the present invention to be described later can contain.

The cosmetic product of the present invention comprises the skin anti-aging agent or the agent for regulating expression of anti-aging related gene. Here, "comprise" means that the cosmetic product may comprise a physiologically acceptable carrier and optional components such as concurrently usable other auxiliary components according to an intended product form.

The cosmetic product of the present invention can be provided as, for example, a skin care cosmetic product or a cosmetic product for hair to be used by applying to the scalp and hair. Note that the cosmetic product in the present invention encompasses quasi-drugs in addition to the cosmetic products of the Pharmaceutical Affairs Law.

When the anti-aging agent or the agent for regulating expression of anti-aging related gene of the present invention is provided as a cosmetic product, the preparable dosage form is not particularly limited as long as applicable to skin. Specifically, the anti-aging agent or the agent for regulating expression of anti-aging related gene can be provided as a lotion, a milky lotion, a cream, a gel, a jelly, an essence, a lip balm, a pack, a mask, or the like in the dosage form of a liquid form, an emulsion form, a gel form, a cream form, an ointment form, a foam form, a mist form, an aerosol form, or the like.

The other optional components that these cosmetic products can contain are not particularly limited and additives that can be mixed in typical cosmetic products can be used. Examples of the additive include water, a fat and an oil, a wax, a hydrocarbon, a fatty acid, an alcohol, an ester, a surfactant, a flavor, an astringent, a germicidal and/or antibacterial agent, a whitening agent, a UV absorber, a moisturizer, a cell activator, an antiphlogistic and/or antiallergic agent, an antioxidant, a vitamin and a natural extract. The contents of these other optional components are not particularly limited either and can be suitably selected according to an intended dosage form, and the like.

Additionally, the anti-aging agent or the agent for regulating expression of anti-aging related gene of the present invention can be provided as food or drink to be used via oral intake. The food and drink encompass health food products (for example, a functional food product, a nutritional supplementary product, a health supplementary product, a nutritionally enriched product, a nutritionally balanced food product, and a supplement), foods with health claims (for example, a food for specified health uses, a food with nutrient function claims, and a food with functional claims), foods for special dietary uses (for example, a food for sick people, a formulated milk powder for infants, and a milk powder for pregnant or lactating mothers), and additionally products categorized as a food and a drink with a label for risk reduction, prevention or improvement of diseases or conditions (symptoms) caused by reduced function of the dermal fibroblast.

The other optional components that these foods and drinks can contain are not particularly limited and additives that can be mixed in typical foods and drinks can be used.

EXAMPLES

Hereinafter, the present invention will be described more specifically in reference to Examples, but the technical scope of the present invention is in no way limited to these examples.

[Example 1] Cell Proliferation Action, Collagen and Hyaluronan Production Promoting Actions 1 Purpose and Overview of the Test Collagen and hyaluronan in the skin are considered to play an important role to the skin firmness, the skin softness and wetness. Accordingly, synergistic effects of test substances (a special low molecular DNA and a soybean extract) were evaluated by the proliferation action on the dermal fibroblast, and the collagen and hyaluronan production promoting actions.

2 Materials and Test Method 2-1 Cell

Human newborn-derived dermal fibroblast cell line NB1RGB cell (RIKEN BRC, Japan) was used and cultured in a $CO_2$ incubator ($CO_2$ concentration of 5%, 37° C.)

2-2 Medium

Eagle's Minimal Essential Medium (EMEM, Wako, Japan) comprising 0.1% (v/v) Fetal Bovine Serum (FBS, Hyclone, UK) and a 1.0% (v/v) antifungal agent (Invitrogen, USA) was used.

2-3 Test Substances (1) Special Low Molecular DNA

A hydrolyzed DNA-Na (powder) manufactured by NISSEI BIO CO., LTD. was used. This product was prepared, by the method described earlier, by extracting a Na salt of DNA from the orchis (milt) of salmonid fish.

Note that analysis results by Gel Permeation Chromatography (GPC) on the hydrolyzed DNA-Na (manufactured by NISSEI BIO CO., LTD.) used are shown in FIG. 1, and the relation between the retention time and the molecular weight is shown in Table 1. A molecular weight reference of 12,000 was based on the retention time of Cytochrome c (MW 12,400).

TABLE 1

| Retention time (min) | <17.0 | 17.0 | 20.0 | 22.0 | 25.0 | 30.0 | 34.0 | 41.0 | >41.0 |
|---|---|---|---|---|---|---|---|---|---|
| Molecular weight reference (M.W) | 20,000 or more | 20,000 | 12,000 | 8,000 | 5,000 | 2,000 | 1,000 | 330 | <330 |
| Base number reference (mer) | >60 | 60 | 36 | 24 | 15 | 6 | 3 | 1 | — |

According to the above analysis results, fractions by the molecular weight of the hydrolyzed DNA-Na (manufactured by NISSEI BIO CO., LTD.) are as follows.

Fractions having a molecular weight of 12,000 to 5,000 (elution time of 20 min to less than 25 min): 32.0%

Fractions having a molecular weight of 5,000 or less (elution time of 25 min and thereafter): 32.4%

From the above, the fractions having a molecular weight of 12,000 or less of the hydrolyzed DNA-Na (manufactured by NISSEI BIO CO., LTD.) are 64.4%.

The test substance (hydrolyzed DNA-Na) adjusted to 3.0 mg/mL using 30 μM L-ascorbic acid (CAS No. 50-81-7, Wako, Japan) and 0.1% FBS-containing EMEM was serially diluted in a common ratio of 10 and prepared to the total of 2 concentrations (0.03 mg/mL, 0.3 mg/mL) when used (final concentrations were 0.01 mg/mL, 0.1 mg/mL).

(2) Soybean Extract

PHYTOPOLYAMINE (registered trademark)-SP (product number: SPA-308, mixing ratio: about 70% of a soybean sprout extract, about 30% of citric acid Na) manufactured by TOYOBO CO., LTD. was used.

The test substance (SPA-308) in concentrations of 0.39 mg/mL, 0.81 mg/mL, and 1.53 mg/mL was prepared when used by using 30 µM L-ascorbic acid (CAS No. 50-81-7, Wako, Japan) and 0.1% FBS-containing EMEM (final concentrations were 0.13 mg/mL, 0.27 mg/mL, and 0.51 mg/mL).

(3) Mixed Solution (Concurrent Use)

Two kinds of the test substances described above were used.

The hydrolyzed DNA-Na adjusted to 3.0 mg/mL using SPA-308-containing EMEM, which was adjusted to 0.81 mg/mL using 30 µM L-ascorbic acid (CAS No. 50-81-7, Wako, Japan) and 0.1% FBS-containing EMEM, was serially diluted in a common ratio of 10 and prepared to the total of 2 concentrations (0.03 mg/mL, 0.3 mg/mL) when used [final concentration of SPA-308 was 0.27 mg/mL and final concentrations of the hydrolyzed DNA-Na were 0.01 mg/mL, 0.1 mg/mL].

2-4 Test Constitution

For the calculation of the cell proliferation, collagen production, and hyaluronan production, an average value of 3 wells per treated group was used. Additionally, the test was carried out with one group each of a test substance administered group and an operational control group per plate. The operations relating to the test including the test substance preparations were carried out at room temperature unless otherwise specified.

2-5 Test Operations (1) Cell Culture

A $2.0 \times 10^4$ cells/200 µL of NB1RGB cells per well were seeded in a 96-well plate (Lot. 3595, Corning, USA) and cultured in a $CO_2$ incubator for 24 hours. Additionally, 200 µL of Phosphate buffer saline (PBS(-), Lot. 198601, Nissui, Japan) was added to wells that were not used for the test to prevent drying during the culture.

24 hours later, 100 µL of the test substance and the negative control were added to the 96-well plate and cultured for 48 hours in the $CO_2$ incubator. For the negative control, 30 µM L-ascorbic acid and 0.1% FBS-containing EMEM were used.

48 hours later, the culture supernatant was dispensed to a new 96-well plate and freeze-dried (−20° C.). A collagen level and hyaluronan level in the culture supernatant were measured using ELISA (Enzyme-Linked Immuno Sorbent Assay) described in 2-5 (3) and (4) to evaluate the collagen and hyaluronan production promoting actions of the test substance. Additionally, the number of cells in the 96-well plate from which the culture supernatant had been removed was counted by the method described in 2-5 (2) to evaluate the cell proliferation action of the test substance.

(2) Cell Proliferation Action

The effects of the test substance on the proliferation of dermal fibroblast were evaluated as follows.

Each well of the 96-well plate from which the medium had been removed was gently washed twice with 300 µL of PBS(-) heated to 37° C. Subsequently, 100 µL of a solution of 3-(4,5-dimethylthiazol-2-yl)-2,5-diphenyltetrazolium bromide (MTT, CAS No. 298-93-1, Sigma-Aldrich, USA) in 0.5 mg/mL per well was added thereto and cultured for 2 hours in a $CO_2$ incubator.

After completion of the culture, the MTT solution was removed and the plate was washed with 200 µL of PBS(-).

200 µL of 2-propanol (CAS No. 67-63-0, Kanto Chemical, Japan) comprising 0.04 N hydrochloric acid (CAS No. 7647-01-0, Kanto Chemical, Japan) was added thereto and allowed to stand for 1 hour under a shading condition to solubilize the produced insoluble formazan.

The 96-well plate was shaken for 10 seconds at 270 rpm to homogeneously disperse the pigment in the well, and then an absorbance at 570 nm ($OD_{570}$) was measured using a microplate reader (SPARK™ 10M, TECAN, Switzerland).

An $OD_{570}$ of the test substance administered group, with the $OD_{570}$ of the negative control being 100%, was calculated as a cell proliferation rate (%). The cell proliferation rates (%) of the negative control and the test substance administered group were subjected to a significance test by unpaired two groups test (Student's t-test). All the tests had significance levels of less than 5% on two sides ($p<0.05$, $p<0.01$, $p<0.001$).

(3) Collagen Production Promoting Action

The effects of the test substance on the production of collagen Type I, which is said to impart the skin with firmness and elasticity, were evaluated by competitive ELISA as follows.

For the measurement of a collagen level in the culture supernatant, Human Collagen type I ELISA kit (Lot. EC1-E105, ACEL, Japan) was used.

A collagen standard solution was serially diluted using Dilution buffer in a common ratio of 2 to prepare the total of 7 concentrations. Additionally, the culture supernatant was diluted two-fold with Dilution buffer.

14 µL of a biotin-labeled collagen antibody solution was added to 126 µL of a collagen standard solution and the two-fold diluted culture supernatant and mixed by tapping.

The collagen immobilized microtiter plate was washed three times with 200 µL of Wash buffer, 50 µL of the standard solution containing biotin-labeled collagen antibody and the culture supernatant were added thereto and shaken for 1 hour at about 270 rpm.

1 hour later, the plate was washed three times with 200 µL of Wash buffer, 50 µL of a peroxidase-labeled avidin solution was added thereto and shaken for 1 hour at about 270 rpm. 1 hour later, the plate was washed three times with 200 µL of Wash buffer, 50 µL of a 3,3',5,5'-tetramethylbenzidine substrate solution per well was added thereto and allowed to stand for 15 minutes.

Then, 50 µL of Stop solution per well was added thereto, the microtiter plate was shaken for 1 minute at 270 rpm to homogenize the pigment in the well, and subsequently an absorbance at 450 nm ($OD_{450}$) was measured using a microplate reader.

A calibration curve was regressed from the $OD_{450}$ of the collagen standard solution using 4-Parameter logistic model. A value obtained from the regression equation was multiplied by a dilution rate to calculate collagen production levels (µg/mL) of the negative control and the test substance.

A collagen production rate (%) of the test substance, with the collagen production level of the negative control being 100%, was calculated. The collagen production rates (%) of the negative control and the test substance added group were subjected to a significance test by unpaired two groups test (Student's t-test). All the tests had significance levels of less than 5% on two sides ($p<0.05$, $p<0.01$, $p<0.001$).

(4) Hyaluronan Production Promoting Action

The effects of the test substance on the production level of hyaluronan, which is said to hold moisture in collagen and elastin, were evaluated by sandwich ELISA as follows.

For the measurement of a hyaluronan level in the culture supernatant, Hyaluronan Quantikine ELISA kit (Lot. DHYAL0, R&D Systems, USA) was used.

A hyaluronan standard solution was serially diluted using Dilution buffer in a common ratio of 2 to prepare the total of 7 concentrations. Additionally, the culture supernatant was diluted eight-fold with Dilution buffer.

To an aggrecan immobilized microtiter plate, 50 μL of a biotin-labeled hyaluronan antibody solution per well was added. Further, 50 μL of the diluted culture supernatant was added thereto and shaken for 1 hour at about 270 rpm.

1 hour later, the plate was washed five times with 400 μL of Wash buffer, 100 μL of a peroxidase-labeled avidin solution was added thereto and shaken for 1 hour at about 270 rpm. 1 hour later, the plate was washed five times with 400 μL of Wash buffer, 100 μL of a 3,3',5,5'-tetramethylbenzidine substrate solution per well was added thereto and allowed to stand for 30 minutes under a shading condition.

Then, 100 μL of Stop solution per well was added thereto, the microtiter plate was shaken for 1 minute at 270 rpm to homogenize the pigment in the well, and subsequently an absorbance at 450 nm ($OD_{450}$) was measured using a microplate reader.

A calibration curve was regressed from the $OD_{450}$ of the hyaluronan standard solution using 4-Parameter logistic model. A value obtained from the regression equation was multiplied by a dilution rate to calculate hyaluronan production levels (ng/mL) of the negative control and the test substance.

A hyaluronan production rate (%) of the test substance, with the hyaluronan production level of the negative control being 100%, was calculated. The hyaluronan production rates (%) of the negative control and the test substance added group were subjected to a significance test by unpaired two groups test (Student's t-test). All the tests had significance levels of less than 5% on two sides ($p<0.05$, $p<0.01$, $p<0.001$).

3 Test Results
3-1 Special Low Molecular DNA
(1) Cell Proliferation Action

The cell proliferation rates ±standard deviation of 0.01 mg/mL and 0.1 mg/mL of the test substance (hydrolyzed DNA-Na) were, with the cell proliferation level ($OD_{570}$) of the negative control being 100%, 101.3±6.8% and 102.6±3.3%, respectively.

(2) Collagen Type I Production Promoting Action

The collagen production rates ±standard deviation of 0.01 mg/mL and 0.1 mg/mL of the test substance (hydrolyzed DNA-Na) were, with the collagen production level of the negative control being 100%, 126.4±7.9% ($p<0.01$) and 134.0±3.6% ($p<0.01$), respectively.

(3) Hyaluronan Production Promoting Action

The hyaluronan production rates ±standard deviation of 0.01 mg/mL and 0.1 mg/mL of the test substance (hydrolyzed DNA-Na) were, with the hyaluronan production level of the negative control being 100%, 102.2±5.0% and 102.9±7.5%, respectively.

3-2 Soybean Extract
(1) Cell Proliferation Action

The cell proliferation rates ±standard deviation of 0.13 mg/mL, 0.27 mg/mL, and 0.51 mg/mL of the test substance (SPA-308) were, with the cell proliferation level ($OD_{57}$) of the negative control being 100%, 111.6±1.0% ($p<0.01$), 123.7±2.4% ($p<0.01$), and 137.0±6.9% ($p<0.01$), respectively.

(2) Collagen Type I Production Promoting Action

The collagen production promotion rates ±standard deviation of 0.13 mg/mL, 0.27 mg/mL, and 0.51 mg/mL of the test substance (SPA-308) were, with the collagen production promoting action of the negative control being 100%, 135.1±1.3% ($p<0.01$), 174.1±6.3% ($p<0.01$), and 199.9±11.8% ($p<0.01$), respectively.

(3) Hyaluronan Production Promoting Action

The hyaluronan production rates ±standard deviation of 0.13 mg/mL, 0.27 mg/mL, and 0.51 mg/mL of the test substance (SPA-308) were, with the hyaluronan production level of the negative control being 100%, 113.1±4.7% ($p<0.01$), 123.3±3.8% ($p<0.01$), and 137.8±10.3% ($p<0.01$), respectively.

3-3 Concurrent Use of the Special Low Molecular DNA and the Soybean Extract
(1) Cell Proliferation Action The cell proliferation rates ±standard deviation of 0.01 mg/mL+0.27 mg/mL and 0.1 mg/mL+0.27 mg/mL of the test substance (hydrolyzed DNA-Na+SPA-308) were, with the cell proliferation level ($OD_{570}$) of the negative control being 100%, 133.0±4.8% ($p<0.01$) and 140.8±5.7% ($p<0.01$), respectively.

(2) Collagen Type I Production Promoting Action

The collagen production rates ±standard deviation of 0.01 mg/mL+0.27 mg/mL and 0.1 mg/mL+0.27 mg/mL of the test substance (hydrolyzed DNA-Na+SPA-308) were, with the collagen production level of the negative control being 100%, 178.1±5.5% ($p<0.01$) and 230.6±9.9% ($p<0.01$), respectively.

(3) Hyaluronan Production Promoting Action

The hyaluronan production rates ±standard deviation of 0.01 mg/mL+0.27 mg/mL and 0.1 mg/mL+0.27 mg/mL of the test substance (hydrolyzed DNA-Na+SPA-308) were, with the hyaluronan production level of the negative control being 100%, 132.7±7.6% ($p<0.01$) and 139.8±2.9% ($p<0.01$), respectively.

The above results are shown in Table 2. In Table 2, "DNA-Na" is "hydrolyzed DNA-Na". Table 2 reveals that the cell proliferation rates, the collagen production rates, and the hyaluronan production rates when the special low molecular DNA (hydrolyzed DNA-Na) and the soybean extract (SPA-308) were concurrently used are notably greater than the sum of degrees (rates) when each component was used independently. These results can confirm the synergistic effects of the special low molecular DNA and the soybean extract on the activating actions on the function of the dermal fibroblast (cell proliferation action, collagen production promoting action, and hyaluronan production promoting action).

TABLE 2

| Test substance | Concentration | Cell proliferation rate (%) | Collagen production rate (%) | Hyaluronan production rate (%) |
|---|---|---|---|---|
| DNA-Na | 0.01 mg/mL | 101.3 ± 6.8 | 126.4 ± 7.9** | 102.2 ± 5.0 |
|  | 0.1 mg/mL | 102.6 ± 3.3 | 134.0 ± 3.6** | 102.9 ± 7.5 |
| SPA-308 | 0.13 mg/mL | 111.6 ± 1.0** | 135.1 ± 1.3** | 113.1 ± 4.7** |
|  | 0.27 mg/mL | 123.7 ± 2.4** | 174.1 ± 6.3** | 123.3 ± 3.8** |
|  | 0.51 mg/mL | 137.0 ± 6.9** | 199.9 ± 11.8** | 137.8 ± 10.3** |

TABLE 2-continued

| Test substance | Concentration | Cell proliferation rate (%) | Collagen production rate (%) | Hyaluronan production rate (%) |
|---|---|---|---|---|
| DNA-Na SPA-308 (Concurrent use) | 0.01 mg/mL 0.27 mg/mL | 133.0 ± 4.8** | 178.1 ± 5.5** | 132.7 ± 7.6** |
| | 0.1 mg/mL 0.27 mg/mL | 140.8 ± 5.7 | 230.6 ± 9.9 | 139.8 ± 2.9** | n = 3,
**P < 0.01
(Concurrent use) Concentration; Upper row: DNA-Na, Lower row: SPA-308

[Example 2] Hyaluronan Synthase or Breakdown Enzyme Gene Expression Regulation

1 Purpose and Overview of the Test

Collagen and hyaluronan in the skin play an important role to the skin firmness, softness and wetness, and it is known that a decrease in a hyaluronan level in the dermis is particularly involved with the reduction of skin elasticity and wrinkle formation. Accordingly, in the present example, effects of the test substances (special low molecular DNA and soybean extract) on the expression of genes related to anti-aging such as synthesis and breakdown of hyaluronan in the dermal fibroblast were evaluated by the Real-Time PCR method.

2 Materials and Test Method 2-1 Cell

The same cells as in 2-1 of Example 1 were cultured under the same conditions and used.

2-2 Medium

Medium (EMEM) having the same composition as in 2-2 of Example 1 was used, with the exception that a content of FBS (Fetal Bovine Serum) was changed to 10.0% (v/v).

2-3 Test Substances (1) Special Low Molecular DNA Solution

The same special low molecular DNA (hydrolyzed DNA-Na) as in 2-3 (1) of Example 1 was used.

The test substance (hydrolyzed DNA-Na) adjusted to 1 mg/mL using 10% FBS-containing EMEM was serially diluted in a common ratio of 10 to prepare the total of 2 concentrations when used (final concentrations of 0.01 mg/mL, 0.1 mg/mL).

(2) Soybean Extract Solution

The same soybean extract (SPA-308) as in 2-3 (2) of Example 1 was used.

The test substance (SPA-308) adjusted to 2.7 mg/mL using 10% FBS-containing EMEM was serially diluted in a common ration of 10 to prepare the total of 2 concentrations when used (final concentrations of 0.027 mg/mL, 0.27 mg/mL).

(3) Mixed Solution (Concurrent Use)

Two of the test substances described above were used.

The hydrolyzed DNA-Na adjusted to 1 mg/mL using SPA-308-containing EMEM adjusted to 0.27 mg/mL using 10% FBS-containing EMEM was serially diluted in a common ration of 10 to prepare the total of 2 concentrations when used (final concentration of SPA-308 was 0.27 mg/mL, final concentrations of hydrolyzed DNA-Na were 0.01 mg/mL, 0.1 mg/mL).

2-4 Gene Expression Analysis

The expression analysis of genes encoding the following enzymes was carried out using TaqMan Assay (Applied Biosystems, USA).

Human Hyaluronan Synthase 1 (HAS1), Assay ID. Hs00758053_m1

Human Hyaluronan Synthase 2 (HAS2), Assay ID. Hs00193435_m1

Human Hyaluronidase 1 (HYAL1), Assay ID. Hs00201046_m1

Human Glyceraldehyde-3-PhosphateDehydrogenase (GAPDH, Assay ID. Hs02786624_g1) gene was used as an internal standard gene.

2-5 Test Constitution

For the analysis of gene expression levels, an average value of 3 sets of 35-mm dish (Cat No. 150318, Thermo Scientific, USA) per treated group was used. The operations relating to the test including the test substance preparations were carried out at room temperature unless otherwise specified.

2-6 Test Method (1) Cell Culture and Test Substance Addition

A $5.0 \times 10^3$ cells/2 mL of NB1RGB cells were seeded in a 35-mm dish and cultured for 24 hours in a $CO_2$ incubator. 24 hours later, the medium in the 35-mm dish was removed, the test substance and negative control-containing medium were added thereto and cultured for 24 hours in a $CO_2$ incubator.

(2) RNA Extraction, and Purification and Quantity Determination

RNA Extraction and purification were carried out as follows using PureLink™ RNA Mini Kit (Cat No. 12183018A, Invitrogen, USA).

After 24-hour culture, the 35-mm dish from which the medium had been removed was washed twice with 2 mL of PBS(−) heated to 37° C. To this, 600 μL of Dithiothreitol-containing Lysis Buffer (CAS No. 27565-41-9, Invitrogen, USA) was added to dissolve the cells and the lysate was collected. Further, cells in the collected lysate were crushed using Homogenizer (Cat No. 12183-026, Invitrogen, USA).

600 μL of a 70% ethanol (CAS No. 64-17-5, Japan Alcohol, Japan) solution was added to the cell-crushed liquid, then the liquid was moved to a silica membrane-based column, which was subsequently centrifuged for 15 seconds at 12,000×g at room temperature, and the filtrate was discarded.

700 μL of guanidine isothiocyanate-containing Wash Buffer and 500 μL of ethanol-containing Wash Buffer II were added to the silica membrane to wash, which was subsequently centrifuged for 15 seconds at 12,000×g at room temperature and dried. 30 μL of RNase-Free Water was added to the membrane and allowed to stand for 1 minute at room temperature, and then the membrane was centrifuged for 15 seconds at 12,000×g at room temperature. This procedure was repeated twice to elute RNA from the membrane.

A part of the eluted RNA was collected separately to a UV permeable 96-well plate (Cat No. 8404, Thermo Scientific, USA) and diluted 25-fold using Tris-EDTA Buffer (TE (pH 8.0), Cat No. 310-90023, NIPPON GENE, Japan) to measure an absorbance at 260 nm ($OD_{260}$) using a microplate reader (SPARK™ 10M TECAN, Switzerland).

RNA concentrations of the negative control and the test substance were calculated using the $OD_{260}$ by the following formula and diluted using TE Buffer to adjust the RNA concentrations to 10 μg/mL.

RNA concentration (μg/mL)=A×K×0.3 (light path length: cm)×25 (dilution rate)

A: $OD_{260}$ of negative control or test substance

K: K=40, absorption coefficient of RNA (3) Gene Expression Analysis by the Real-Time PCR Method Reverse transcription of RNA was carried out as follows using SuperScript™ IV VILO™ Master Mix with ezDNase (Cat No. 11766050, Invitrogen, USA).

1 μL of 10× ezDNase Buffer, 1 μL of ezDNase enzyme, 6 μL of Nuclease-free Water, and 2 μL of 10 μg/mL RNA per well were added to an 8-tube strip (AB1182, Thermo Scientific, USA) and incubated for 2 minutes at 37° C. 2 minutes later, 4 μL of SuperScript™ IV VILO™ Master Mix and 6 μL of Nuclease-free Water per well were added to the 8-tube strip and heated for 10 minutes at 25° C., 10 minutes at 50° C., and 5 minutes at 85° C. to synthesize cDNA using a Real-Time PCR (QuantStudio™3, Applied Biosystems, USA).

10 μL of TaqMan™ Fast Advanced Master Mix (Cat No. 4444557, Applied Biosystems, USA), 1 μL of TaqMan Gene Expressior, 7 μL of UltraPure™ Distilled Water (Invitrogen, Cat No. 10977-015, USA), and 2 μL of cDNA per well were added to a PCR plate (Cat No. N8010560, Thermo Scientific, USA) and the plate was hermetically sealed using a plate seal (Cat No. 4360954, Thermo Scientific, USA).

The solution was spun down using a plate centrifuge, foams were removed, and then Real-Time qPCR was carried out using a Real-Time PCR system to calculate a Threshold Cycle (Ct) value, which is the number of cycles at which a fluorescence signal of each gene of the negative control and the test substance crosses any threshold. A Ct value was corrected to be a ΔCt value using the internal standard gene. The ΔCt value was corrected to be a ΔΔCt value using an average of the ΔCt values of the negative controls. Assuming that a difference of the detection per cycle by the ΔΔCt method is two times the volume in difference, a gene expression level of the test substance was analyzed by assigning to $2^{-\Delta\Delta Ct}$ when the gene expression level of the negative control is 1. Gene expression levels of the negative control and the test substance added group were subjected to a significance test by paired two groups test (paired t-test). All the tests had significance levels of less than 5% on two sides ($p<0.05$, $p<0.01$, $p<0.001$).

3 Test Results 3-1 Special Low Molecular DNA (1) Human Hyaluronan Synthase 1 Gene (HAS1) Expression The HAS1 expression levels ±standard deviation of 0.01 mg/mL and 0.1 mg/mL of the test substance (hydrolyzed DNA-Na) were, with the HAS1 expression level of the negative control being 1, 1.11±0.04 and 1.02±0.07, respectively.

(2) Human Hyaluronan Synthase 2 Gene (HAS2) Expression

The HAS2 expression levels ±standard deviation of 0.01 mg/mL and 0.1 mg/mL of the test substance (hydrolyzed DNA-Na) were, with the HAS2 expression level of the negative control being 1, 1.25±0.09 ($p<0.05$) and 1.49±0.05 ($p<0.001$), respectively.

(3) Human Hyaluronidase 1 Gene (HYAL1) Expression

The HYAL1 expression levels ±standard deviation of 0.01 mg/mL and 0.1 mg/mL of the test substance (hydrolyzed DNA-Na) were, with the HYAL1 expression level of the negative control being 1, 1.06±0.12 and 1.34±0.14, respectively.

3-2 Soybean Extract (1) Human Hyaluronan Synthase 1 Gene (HAS1) Expression

The HAS1 expression levels ±standard deviation of 0.027 mg/mL and 0.27 mg/mL of the test substance (SPA-308) were, with the HAS1 expression level of the negative control being 1, 1.03±1.2 and 0.99±0.16, respectively.

(2) Human Hyaluronan Synthase 2 Gene (HAS2) Expression

The HAS2 expression levels ±standard deviation of 0.027 mg/mL and 0.27 mg/mL of the test substance (SPA-308) were, with the HAS2 expression level of the negative control being 1, 1.88±0.46 ($p<0.05$) and 1.50±0.11 ($p<0.01$), respectively.

(3) Human Hyaluronidase 1 Gene (HYAL1) Expression

The HYAL1 expression levels ±standard deviation of 0.027 mg/mL and 0.27 mg/mL of the test substance (SPA-308) were, with the HYAL1 expression level of the negative control being 1, 0.97±0.08 and 0.84±0.06, respectively.

3-3 Concurrent Use of the Special Low Molecular DNA and the Soybean Extract (1) Human Hyaluronan Synthase 1 Gene (HAS1) Expression The HAS1 expression levels ±standard deviation of 0.01 mg/mL+0.27 mg/mL and 0.1 mg/mL+0.27 mg/mL of the test substance (hydrolyzed DNA-Na+SPA-308) were, with the HAS1 expression level of the negative control being 1, 0.99±0.08 and 1.51±0.26 ($p<0.05$), respectively.

(2) Human Hyaluronan Synthase 2 Gene (HAS2) Expression

The (HAS2) expression levels ±standard deviation of 0.01 mg/mL+0.27 mg/mL and 0.1 mg/mL+0.27 mg/mL of the test substance (hydrolyzed DNA-Na+SPA-308) were, with the (HAS2) expression level of the negative control being 1, 1.41±0.10 ($p<0.01$) and 1.54±0.07 ($p<0.001$), respectively.

(3) Human Hyaluronidase 1 Gene (HYAL1) Expression

The (HYAL1) expression levels ±standard deviation of 0.01 mg/mL+0.27 mg/mL and 0.1 mg/mL+0.27 mg/mL of the test substance (hydrolyzed DNA-Na+SPA-308) were, with the (HYAL1) expression level of the negative control being 1, 0.58±0.11 ($p<0.01$) and 0.93±0.05, respectively.

The results described above are shown in Table 3. In Table 3, "DNA-Na" is "hydrolyzed DNA-Na". Table 3 reveals that when the special low molecular DNA (hydrolyzed DNA-Na) and the soybean extract (SPA-308) were used concurrently, the expression level of Human Hyaluronan Synthase-1 gene (HAS1) synergistically increases and the expression level of Human Hyaluronan Synthase-2 gene (HAS2) significantly increases compared to those of the negative control. Further, it is revealed that the expression level of Human Hyaluronidase 1 gene (HYAL1) synergistically decreases. These results can confirm that when the special low molecular DNA (hydrolyzed DNA-Na) and the soybean extract (SPA-308) are used concurrently, the promotion of the expression of genes related to hyaluronan synthesis and the decrease in the expression of genes related to hyaluronan breakdown occur simultaneously.

TABLE 3

| Test substance | Concentration | Human Hyaluronan Synthase 1 gene (HAS1) | Human Hyaluronan Synthase 2 gene (HAS2) | Human Hyaluronidase 1 gene (HYAL1) |
|---|---|---|---|---|
| DNA-Na | 0.01 mg/mL | 1.11 ± 0.04 | 1.25 ± 0.09* | 1.06 ± 0.12 |
|  | 0.1 mg/mL | 1.02 ± 0.07 | 1.49 ± 0.05*** | 1.34 ± 0.14 |
| SPA-308 | 0.027 mg/mL | 1.03 ± 1.2 | 1.88 ± 0.46* | 0.97 ± 0.08 |
|  | 0.27 mg/mL | 0.99 ± 0.16 | 1.50 ± 0.11** | 0.84 ± 0.06 |
| DNA-Na SPA-308 (Concurrent use) | 0.01 mg/mL 0.27 mg/mL | 0.99 ± 0.08 | 1.41 ± 0.10** | 0.58 ± 0.11** |
|  | 0.1 mg/mL 0.27 mg/mL | 1.51 ± 0.26* | 1.54 ± 0.07*** | 0.93 ± 0.05 | n = 3,
*$P < 0.05$,
**$P < 0.01$,
***$P < 0.001$
(Concurrent use) Concentration; Upper row: DNA-Na, Lower row: SPA-308

The above results suggest that the synergistic production increases of collagen and hyaluronan when the special low molecular DNA (hydrolyzed DNA-Na) and the soybean extract (SPA-308) were used concurrently shown in Example 1 is caused by the simultaneous occurrence of the promotion of the expression of the genes related to synthesis of collagen and hyaluronan and the decrease in the expression of the gene related to breakdown thereof.

INDUSTRIAL APPLICABILITY

The skin anti-aging agent of the present invention has different actions and functions from conventional anti-aging agents and is more capable of efficiently preventing and/or improving the skin aging than conventional anti-aging agents and thus particularly useful in the field of cosmetic products.

The invention claimed is:

1. A method for activating a function of a dermal fibroblast comprising:
  applying a composition comprising a special low molecular DNA extracted and purified from an orchis of fish, and a soybean extract as active ingredients to a subject in need of activating the function of a dermal fibroblast, wherein
  the special low molecular DNA is a hydrolysate of DNA, and contains 10 to 80% of fractions having a molecular weight of 330 to 12,000;
  the soybean extract is an extract of at least one selected from the group consisting of soybean seeds, germs, and sprouts;
  a content of the special low molecular DNA is 0.001 to 0.5% by mass, a content of the soybean extract is 0.01 to 0.5% by mass, and a content ratio of the special low molecular DNA and the soybean extract is 1:10 to 5:1; and
  the activation of the function is at least one action selected from the group consisting of a proliferation-promoting action, a collagen Type I production-promoting action, and a hyaluronan production-promoting action on a dermal fibroblast.

2. A method for regulating gene expression of a dermal fibroblast comprising:
  applying a composition comprising a special low molecular DNA extracted and purified from an orchis of fish, and a soybean extract as active ingredients to a subject in need of regulating gene expression of a dermal fibroblast, wherein:
  the special low molecular DNA is a hydrolysate of DNA, and contains 10 to 80% of fractions having a molecular weight of 330 to 12,000;
  the soybean extract is an extract of at least one selected from the group consisting of soybean seeds, germs, and sprouts;
  a content of the special low molecular DNA is 0.001 to 0.5% by mass, a content of the soybean extract is 0.01 to 0.5% by mass, and a content ratio of the special low molecular DNA and the soybean extract is 1:10 to 5:1; and
  the regulation of gene expression is promotion of gene expression of either one of or both of Human Hyaluronan Synthase 1 gene, and Human Hyaluronan Synthase 2 gene of dermal fibroblast, or decrease of gene expression of Human Hyaluronidase 1 gene of dermal fibroblast.

\* \* \* \* \*